United States Patent [19]
Shamoun et al.

[11] Patent Number: 5,985,648
[45] Date of Patent: Nov. 16, 1999

[54] FUSARIUM AVENACEUM AND ITS USE AS BIOLOGICAL CONTROL AGENT FOR RUBUS SPECIES

[75] Inventors: Simon Francis Shamoun; Carmen Oleskevich, both of Victoria, Canada

[73] Assignee: Her Majesty the Queen in right of Canada, as represented by the Minister of Natural Resources, Ottawa, Canada

[21] Appl. No.: 09/086,346

[22] Filed: May 29, 1998

[51] Int. Cl.$^6$ .............................. C12N 1/14; A01N 63/00
[52] U.S. Cl. ................. 435/256.5; 435/929; 424/93.5
[58] Field of Search ................. 424/93.5; 435/256.5, 435/929

[56] References Cited

U.S. PATENT DOCUMENTS 5,635,444  6/1997  Walker et al. ........................ 504/117

OTHER PUBLICATIONS

Abbas et al., Mycotoxins produced from fungi isolated from foodstuffd and soil: comparison of toxicity in fibroblasts and rat feeding tests', Applied and Environmental Microbiology, 1984, vol. 48, No. 3, pp. 654–661.

Shamoun et al., "*Hainesia lythri.* a possible biocintrol agent for thimbleberry in British Columbia forests", Phytophtology, 1992, 80:1080, A161 (Abstract).

Gardner D.E., "Leaf rust caused by *Kuehneola uredinis* on native and nonnative Rubus species in Hawaii", Plant Disase, 1983, vol.67, No.9, pp. 962–963.

Abbas et al., "Bioherbicidal potential of *Fusarium moniliforme* and its phytotoxin, fumonisin", WeedScience, 1991, vol. 39, pp.673–677.

Pitt et al., "Glyphosate efficacy on eastern Canadian forest weeds," Can. J. For. Res., 1992, vol. 22, pp. 1160–1171.

*Primary Examiner*—Sandra E. Saucier
*Assistant Examiner*—Vera Afremova
*Attorney, Agent, or Firm*—J. Wayne Anderson

[57] ABSTRACT

The invention disclosure relates to a biologically pure isolate of *Fusarium avenaceum* ATCC 200684 to a herbicidal composition containing the isolate as active ingredient, and to a method of combating weeds, particularly the Rubus species, comprising applying an effective amount of the composition, thereto.

19 Claims, 3 Drawing Sheets

FUSARIUM AVENACEUM AND ITS USE AS BIOLOGICAL CONTROL AGENT FOR RUBUS SPECIES

BACKGROUND OF THE INVENTION

This invention relates to *Fusarium avenaceum*, to a method for its production, and to its use as a herbicide for Rubus species.

The discovery and development of potential biological control agents to suppress competing forest vegetation is receiving increased attention in the management of conifer regeneration sites. Development of alternatives to commonly used weed control methods, such as herbicide applications and manual cutting, has become important in forest management plans due to economical constraints and increasing public concern over pesticide use. Biological control strategies which utilize microbial organisms or their secondary metabolites to control weeds have been widely investigated on agricultural crops. In forest renewal sites, biological control agents need to be sufficiently virulent to suppress competing vegetation that is often diverse in growth habit and density, while allowing for vegetation to resume its role in forest ecosystems once conifer release has been obtained.

Invasive Rubus species, namely wild red raspberry [*Rubus strigosus* Michx.=*R. idaeus* var. *strigosus* (Michx.) Focke], thimbleberry (*R. parviflorus* Nutt.), and salmonberry (*R. spectabilis* Pursh), are among the top 20 forest weeds in Canada. These native Rubus species can effectively outcompete newly planted or naturally regenerated conifers in reforestation sites in Canada and the northern United States, and reduce the growth and survival of black and white spruce. These Rubus species are perennial, deciduous shrubs which form monospecific, multi-layered shrub communities with long-lived clonal root systems.

DESCRIPTION OF THE PRIOR ART

Previous biological control research to reduce competing Rubus species worldwide has employed various approaches: the inoculative strategy of introducing exotic pathogens, the inundative strategy of using indigenous pathogens, and the biorational strategy of using phytotoxic microbial compounds. The inoculative approach successfully utilized two rust fungi, *Phragmidium violaceum* (Schultz) Winter and *Kuehneola uredinis* (Lk.) Arth., to control exotic or naturalized Rubus species in Australia, New Zealand, Chile, and Hawaii (Gardner [1], Bruzzese & Hasan [2]) Inundative applications of three indigenous fungal pathogens, *Septoria rubi* West., *Cylindrocarpon destructans* (Zinf.) Scholten, and *Hainesia lythri* (Desm.) Höhnel, were effective against *R. parviflorus* when inoculum was formulated or when plant resistance was weakened by prior mechanical or chemical wounding (Wall & Shamoun [3], Shamoun & Callan [4]). The biorational approach has utilized bialaphos, a phytotoxin produced by *Streptomyces viridochromogens*, to successfully reduce height and resurgence of *R. strigosus* in *Picea mariana* plantations in eastern Quebec (Jobidon [5]).

SUMMARY OF THE INVENTION

According to one aspect of the invention, a biologically pure isolate of *Fusarium avenaceum*, having the identifying characteristics of ATCC Deposit no. 200684, is provided.

The isolate was deposited, with the American Type Culture Collection (ATCC), Rockville, Md., 20852, USA, on Sep. 26, 1996, under Accession no. 200684, and was converted to a Budapest Treaty Deposit on Mar. 3, 1998. The viability of the isolate was tested and found viable by the ATCC, on Mar. 13, 1998.

According to another aspect of the invention, a herbicidal composition is provided, containing as active ingredient, *Fusarium avenaceum*, having the identifying characteristics of ATCC Deposit no. 200684.

According to yet another aspect of the invention, a method for combating weeds is provided, comprising applying to a weed plant, an effective amount of a herbicidal composition containing as active ingredient, a biologically pure isolate of *Fusarium avenaceum*, having the identifying characteristics of ATCC Deposit no. 200684.

Preferably, the active ingredient is provided as an aqueous suspension of an agriculturally acceptable sterile granular growth substrate, capable of supporting the growth of the fungus, infested therewith, and an adjuvant.

Most preferably, the adjuvant is an organosilicone surfactant, sold under the trademark Silwet L-77, and the substrate is a cereal grain, e.g., rice.

It will be appreciated by those skilled in the art that various amendments which aid in fungal survival and growth, and facilitate fungal dispersal and adhesion to plant surfaces may also be included, such as nutrients, humectants, invert emulsions and dispersing agents.

DETAILED DESCRIPTION OF THE INVENTION

Materials and Methods

Isolation and Selection of Fungi

Figure 1:
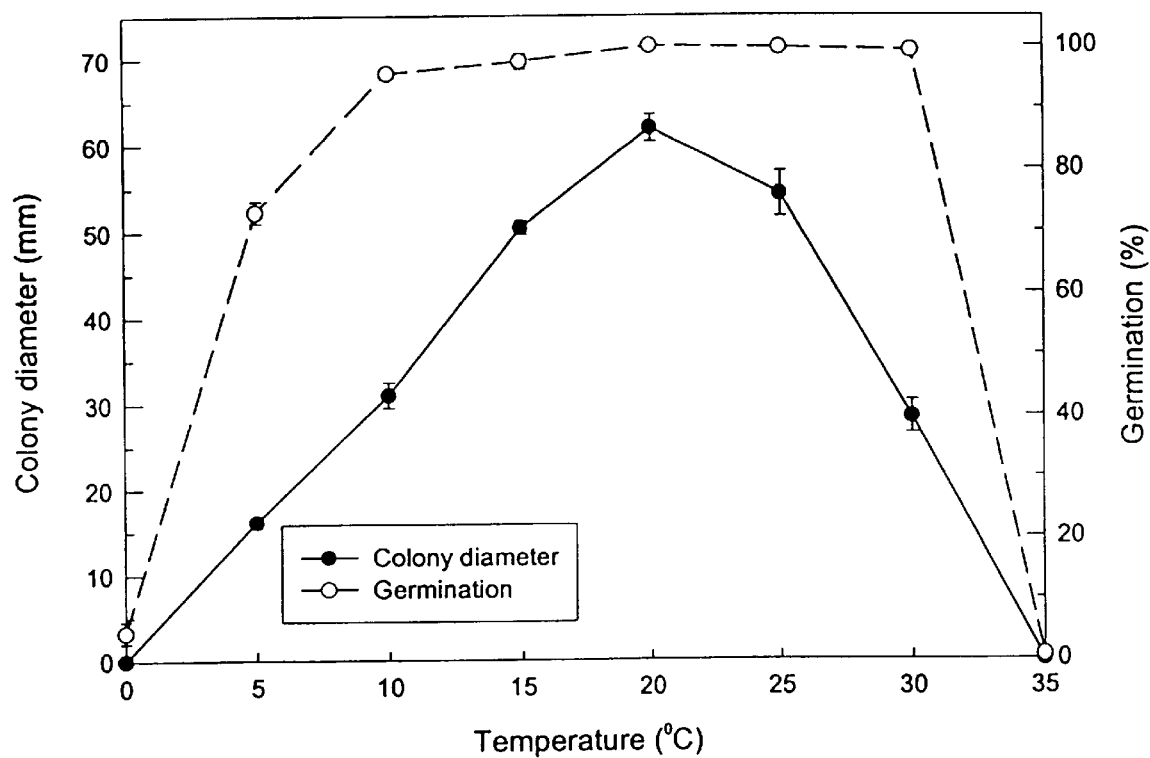
FIG. 1 is a graph illustrating the effect of temperature on *Fusarium avenaceum* growth, and spore germination.
Figure 2:
FIG. 2 is a fulltone illustrating disease symptoms on *Rubus strigosus* plants after inoculation with *Fusarium avenaceum* composition according to the invention.
Figure 3:
FIG. 3 is a fulltone illustrating a comparison of *Rubus strigosus* plants inoculated with *Fusarium avenaceum* composition according to the invention, versus a control.

Samples of foliage and stems of *R. strigosus*, *R. parviflorus*, and *R. spectabilis* with disease symptoms such as anthracnose, foliar and stem lesions, necrosis, shoot blight, and dieback were collected from central (49° to 54° latitude) and coastal (including coastal mainland and Vancouver Island) British Columbia from May to September, 1990–1994. Samples were obtained from the following biogeoclimatic zones: Coastal Douglas-fir, Coastal Western Hemlock, Interior Cedar-Hemlock, Interior Douglas-fir, Montane, and Sub-Boreal Spruce. Diseased plant tissues were excised (ca. 0.25 cm$^2$ sections) and surface-disinfested by successive 1 min rinses in 95% ethanol, 0.525% sodium hypochlorite (w/v) and 3 rinses in sterile distilled water. Tissues were blotted on sterile filter paper, aseptically plated onto malt extract or potato dextrose agar (MEA, PDA, Difco Laboratories, Detroit, Mich.), and incubated at 20–25° C. with a ca. 12 h light/dark cycle. Resulting fungal colonies were subcultured from hyphal tips and pure cultures were stored on MEA and PDA slants and in sterile distilled water at 5° C., with periodic testing for viability. For subsequent testing, minimum subculturing was done and fungi were inoculated onto Rubus hosts and re-isolated when necessary.

Twenty isolates were evaluated for pathogenicity by inoculating detached leaves of Rubus species obtained from shadehouse-grown plants. Test plants were grown from field rootstocks (after cold stratification for 3 months at 0° C.) by planting 10 cm-long root segments in a peat-perlite (1:2, v/v) medium and placing in a mist chamber. Healthy plants were transplanted and maintained at an average height of 0.5 m in 1 gallon pots in peat-vermiculite-sand (3:1:1) medium with a low rate of slow release fertilizer (18-7-12 Osmocote, Grace Sierra, Milipitas, Calif.) in an outdoor shadehouse. Additional plants were later propagated from Rubus stem cuttings by dipping 10-cm long stem segments with two leaves in 0.4% indole-3 butyric acid rooting powder (Stimroot No. 2, Plant Products Ltd., Bramalea, ON) and planting in soil mixtures as above. Mature plants were maintained in the greenhouse at 18–21° C., with ca. 60% relative humidity and a 16 h photoperiod.

Detached Rubus leaves were placed on moistened filter paper (9-cm diameter) in glass Petri plates and inoculated with mycelial plugs (1 cm$^2$), taken from 7-day old colonies, with 3 replicates per isolate, and incubated on the lab bench for 7 days. Control leaves were inoculated with sterile MEA or PDA plugs under identical conditions and often remained green for up to 7 days. Percent leaf area damaged was assessed visually by using the area-addition method in which percent necrosis within leaf quadrants was added cumulatively and the mean percentage was calculated per leaf. Values>50% were considered to indicate strong pathogenicity. An isolate of *F. avenaceum* was selected from these screening tests after causing >50% leaf area necrosis within 7 days.

Colony Growth and Spore Germination

Temperatures ranging from 0–35° C., in 5° C. increments, were used to determine optimum colony growth and spore germination. Fungal colonies were initiated from 5-mm diameter mycelial plugs on PDA and grown under dark conditions for 7 days. For germination tests, conidia were obtained from sporulating colonies on MEA or PDA by flooding plates with sterile distilled water and gently scraping the surface. Conidial suspensions were diluted and spread onto 2% water agar plates, incubated under dark conditions, and percent germination was recorded at 24 h with a total of 300 spores counted at each temperature. For both tests, there were 3–5 replicate plates of each fungus at each temperature and the experiments were repeated.

Inoculum Production

Several agar and liquid media were evaluated for their ability to promote sporulation, as determined by hemacytometer counts, and the following media were selected. *Fusarium avenaceum* was grown in modified Richard's V-8 broth, infested with two mycelial plugs (5 mm) per 250 mL broth, and maintained on a continuous shaker at 100 rpm at 20–22° C. with a 12 h light/dark regime. Agar plates were infested with one mycelial plug (5 mm) taken from actively growing colonies and incubated at 20–22° C., with an alternating 12 h light/dark regime.

Grain substrates, namely rice, millet, and barley, were also evaluated as growth media and were prepared following procedures outlined by Abbas et al.[6]. Specifically, sterile grains are infested with FA and incubated at 20–22 ° C. under optimum light and humidity conditions, with daily shaking. After 2–5 weeks, grains were air-dried and stored at cool temperature. The grains were then ground to a coarse powder (0.1 to 5 mm), resuspended in sterile water (optimum 5 g of substrate per 50 ml of water), sonicated and filtered to obtain culture filtrates for subsequent use.

Pathogenicity Tests

Inundative applications of conidial inoculum were made to Rubus plants exposed to exterior temperature and light conditions in shadehouse trials. Inoculum of each fungus consisted of $10^6$ spores/mL combined with 2% sucrose and 0.5% gelatin and was sprayed onto test plants with a hand-held sprayer (Garden Sprayer, Greenleaf Products Inc., Burnaby, BC) at a rate of 50 mL/$m^2$. A 24 h dew period, provided by covering plants with a clear plastic bag, was included to enhance germination and infection. Plants were rated for extent of necrosis by dividing the plant into quadrants, adding cumulatively the percent necrotic area per quadrant, and calculating the mean percent necrosis per plant. Foliar necrosis was determined on a scale of 0–4 where: 0=no injury, 1=<1% injury, 2=1–10% injury, 3=11–50% injury, 4=51–100% injury. An injury index was subsequently calculated as follows: (summation of [severity ratings×#plants in that class])/total #plants (Yang et al. [7]) with ratings of <2 indicating slight injury, 2–3.5 indicating moderate injury, and >3.5 indicating severe injury. Plants were rated for up to 3 weeks after inoculation and compared to control treatments of water, with 2–3 replicate plants per treatment, and the experiment was repeated. Re-isolations of fungi from treated plants was attempted following methods described previously. Treatment data were combined and subjected to one-way analysis of variance to test for differences between treatment means, followed by the Student-Newman-Keuls test at P=0.05.

ADJUVANTS

Adjuvants were included in the inoculum in an effort to increase pathogenicity. Adjuvants were evaluated individually when combined with spore suspensions ($10^6$ spores/mL) produced on media as described above. Amended inoculum was applied as a central, 100 $\mu$L drop onto detached Rubus leaves, incubated as described for pathogenicity screening tests, and evaluated for necrotic area over 7 days. Inoculum viability was verified by plating on MEA or PDA. Control treatments consisted of spore suspensions or adjuvants, and water. *Fusarium avenaceum* was grown in liquid media and combined separately with 1% malt broth (Difco Laboratories, Detroit, Mich.), 1% neopeptone (Sigma Chemical Co., St. Louis, Mo.), and 1% sodium alginate (BDH Inc., Toronto, ONT), or grown on rice media and combined with 0.2% v/v and 0.4% v/v Silwet L-77[R] (organosilicone surfactant, Loveland Ind., Greeley, Colo.). Among all of these formulations, those which resulted in >50% necrosis were further tested on intact plants as described above. Tests on whole plants were repeated, with 2–3 replicate plants per test, and treatment results were subjected to statistical analysis as described above.

For use with a granular substrate, culture filtrates from above were combined with an organosilicone surfactant e.g. Silwet-L-77, or other adjuvants to produce an inoculum. In this test, FA+0.4% v/v Silwet (see Table 1, below) was effected. The inoculum was sprayed onto Rubus plants at 50 ml/$m^2$ . Foliar necrosis was determined as described above.

Amendment with Glyphosate

The effect of glyphosate (Roundup®, Monsanto Canada Inc., Sardis, BC) on fungal growth on PDA was determined by adding concentrations of up to 6 mM glyphosate or 0.06% filter-sterilized (0.2 $\mu$M) Roundup®. Amended plates were inoculated with a mycelial plug (5 mm) taken from actively growing colonies of the three fungi and incubated at 20° C. Colony diameter was measured at 7 days from 4–6 replicate plates per treatment and the experiment was repeated. Colonies were further assessed for conidial germination after 2–3 weeks, as previously described.

In shadehouse trials, *R. parviflorus* and *R. spectabilis* were treated with glyphosate [2 mM or 6 mM glyphosate (0.02% v/v or 0.06% v/v Roundup®)] (10-fold less than the recommended dose of Roundup® for Rubus species), applied at 50 mL/m², followed by inoculation after 24 hr with spore suspensions (10⁶ spores/mL, obtained from colonies in liquid and agar media) amended with 0.02% v/v Tween 80, applied at the same rate. Plants were visually rated for percent necrotic leaf area over a 3-week period as described previously and compared to control treatments of spore suspensions, glyphosate, or water. For each treatment, three replicate plants were included and the experiment was repeated and data collected was subjected to statistical analysis as described above.

Results and Discussion

The cultures of *F. avenaceum* isolated from field collections and tested on detached Rubus leaves, caused >50% necrosis in 7 days. *Fusarium avenaceum* was collected from stem lesions on *R. strigosus* in the Sub-Boreal Spruce biogeoclimatic zone. Maximum colony growth and spore germination was observed between 10–30° C. and 15–25° C., respectively, for *F. avenaceum* (FIG. 1).

On Rubus plants in shadehouse trials, *F. avenaceum* gave sufficient and reproducible foliar necrosis.

*Fusarium avenaceum*, when grown on rice grains and combined with 0.4% v/v Silwet L-77®, induced greater foliar necrosis on the Rubus spp. than any other fungus or treatment tested. Treated foliage developed a water-soaked appearance, followed by the development of extensive foliar necrosis, within 24–48 h on *R. strigosus* and *R. parviflorus*. This resulted in large areas of necrotic leaf tissue, leaf curl and death (FIGS. 2 & 3). *Rubus strigosus* was the most susceptible to the *F. avenaceum*+Silwet treatment, with 89% of plants demonstrating 51–100% injury within 7 d of treatment (Table 1). On *R. parviflorus, F. avenaceum*+Silwet caused 11–50% injury and 51–100% injury on 44% of plants, respectively. Only 6.25% of *R. spectabilis* test plants showed >50% injury with a similar treatment. Analysis of variance followed by the Student-Newman-Keuls test indicated significant differences between the *F. avenaceum*+ Silwet treatment and all other treatments for *R. strigosus* (F=61.39, P=<0.001), *R. parviflorus* (F=38.43, P=<0.001) and *R. spectabilis* plants (F=12.39, P=<0.001) (Table 1, below). With *R. spectabilis*, increasing the surfactant dosage to 1% v/v Silwet L-77® did not result in increased foliar necrosis. *Fusarium avenaceum* was re-isolated from necrotic leaf tissue of inoculated plants of each Rubus spp. and was not isolated from control plants. All treated plants flushed new leaves by 3 weeks, and the new foliage and stems were free of necrotic symptoms.

TABLE 1

Foliar necrosis of Rubus plants resulting from inundative applications of *Fusarium avenaceum* inoculum, originating from infested rice cultures, and combined with an organosilicone surfactant (0.4% v/v Silwet L-77®).

| | Foliar injury* | | |
|---|---|---|---|
| Treatment | *Rubus strigosus* | *Rubus parviflorus* | *Rubus spectabilis* |
| Control-water | 0.44 ± 0.18 d | 0.20 ± 0.13 c | 0.20 ± 0.13 b |
| Surfactant | 1.89 ± 0.26 b | 2.17 ± 0.31 b | 0.67 ± 0.21 b |
| *F. avenaceum* | 1.33 ± 0.17 c | 1.38 ± 0.38 b | 0.75 ± 0.25 b |
| *F. avenaceum* + surfactant | 3.89 ± 0.11 a | 3.31 ± 0.18 a | 2.00 ± 0.26 a |

*Foliar injury rating index with <2 = slight injury, 2–3.5 = moderate injury, and >3.5 = severe injury. A one-way analysis of variance comparing treatment means was performed. Within a column, means ± standard error of the mean followed by the same letter are not significantly different according to the Student-Newman-Keuls test at P = 0.05.

A preliminary host range test has demonstrated that several economically important conifer seedlings did not display disease symptoms when inoculated with the *F. avenaceum*-Silwet L-77® formulation.

Glyphosate affected fungal growth since the fungi developed irregular colony margins, compared to the even mycelial margin observed in the controls, when grown on PDA amended with up to 6 mM glyphosate. Colony diameters on PDA reached 50% of controls at concentrations of >1 mM glyphosate after 7 days. *Fusarium avenaceum* sporulated on PDA with 0–2 mM glyphosate and conidia germinated readily at 25° C. When low doses of glyphosate were applied to intact plants, followed by fungal inoculation, [a temporary or not significantly greater percent necrosis on Rubus species was observed (*R. parviflorus*; F=16.293, P=<0.001; *R. spectabilis*; F=12.44, P=<0.001) (Table 2, below)] During the treatment evaluation period (3 weeks), all plants receiving glyphosate showed increasing necrosis over time with symptoms of chlorosis (particularly in young leaves), wilting, and low vigour, indicating susceptibility to very low doses of the herbicide.

TABLE 2

Effect of *Fusarium avenaceum* spore suspensions ($10^6$ spores/mL, produced in liquid media), applied alone and in a delayed application following low doses of glyphosate (Roundup®), on foliar necrosis of Rubus species.

| | Foliar injury* | |
|---|---|---|
| Treatment | *Rubus parviflorus* | *Rubus spectabilis* |
| Control-water | 0.29 ± 0.18 d | 0.13 ± 0.13 d |
| 0.02% Roundup ® | 1.71 ± 0.42 bc | 1.83 ± 0.31 ab |
| 0.06% Roundup ® | 2.67 ± 0.33 ab | 1.40 ± 0.40 bc |
| *F. avenaceum* | 1.38 ± 0.38 c | 0.50 ± 0.27 cd |
| *F. avenaceum* + 0.02% v/v Roundup ® | 3.60 ± 0.40 a | 2.50 ± 0.43 ab |
| *F. avenaceum* + 0.06% v/v Roundup ® | 3.83 ± 0.17 a | 2.71 ± 0.36 a |

*Foliar injury rating index with <2 = slight injury, 2–3.5 = moderate injury, and >3.5 = severe injury. A one-way analysis of variance comparing treatment means was performed. Within a column, means ± standard error of the mean followed by the same letter are not significantly different according to the Student-Newman-Keuls test at P = 0.05.

Based on this research, *F. avenaceum* inoculum produced on rice appears to have several suitable attributes for further evaluation as a candidate biological control agent for Rubus species. These include a suitable production method for large amounts of inoculum, a formulation requiring no dew period, a spray method for application, and extensive foliar damage to *R. strigosus* and *R. parviflorus*.

BIBLIOGRAPHY

1. Gardner, D. E. 1983. Leaf rust caused by *Kuehneola uredinis* on native and non-native Rubus species in Hawaii. Plant Dis. 67:962–963.
2. Bruzzese, E., and S. Hasan. 1986. Host specificity of the rust *Phragmidium violaceum*, a potential biological control agent of European blackberry. Ann. Appl. Biol. 108:585–596.
3. Wall, R. E., and S. F. Shamoun. 1990. Experiments on vegetation control with native pathogenic fungi in the southern interior of British Columbia. Can. Forest Serv. and BC Min. of Forests, Forest Resources Development Agreement Rep. 134., Victoria, BC. 18 pp.
4. Shamoun, S. F., and B. E. Callan. 1992. *Hainesia lythri*, a possible biocontrol agent for thimbleberry (*Rubus parviflorus*) in British Columbia forests. Phytopathology 80:1080. (Abstr.).
5. Jobidon, R. 1991. Potential use of bialaphos, a microbially produced phytotoxin, to control red raspberry in forest plantations and its effect on black spruce. Can. J. For. Res. 21:489–497.
6. Abbas, H. K, C. D. Boyette, R. E. Hoagland, and R. F. Vesonder. 1991. Bioherbicidal potential of *Fusarium moniliforme* and its phytotoxin, fumonisin. Weed Sci. 39:673–677.
7. Yang, S. -M., Johnson, D. R., Dowler, W. M., and Connick, W. J., Jr. 1993. Infection of leafy spurge by *Altemaria altemata* and *A. angustiovoidea* in the absence of dew. Phytopathol. 83:953–958.

We claim:

1. A biologically pure isolate of *Fusarium avenaceum*, having all of the identifying characteristics of ATCC Deposit no. 200684.

2. A herbicidal composition, containing as active ingredient, *Fusarium avenaceum*, having all of the identifying characteristics of ATCC Deposit no. 200684.

3. A composition according to claim 2, wherein the active ingredient is provided as an aqueous suspension of an agriculturally acceptable sterile granular growth substrate inoculated therewith, and an adjuvant.

4. A composition according to claim 3, wherein the adjuvant is an organosilicone surfactant, included in an amount of 0.2 to 0.4% v/v.

5. A composition according to claim 4, wherein the amount of the adjuvant is about 0.4% v/v.

6. A composition according to claim 4, wherein the growth substrate is a cereal grain.

7. A composition according to claim 6, wherein the cereal grain is rice.

8. A composition according to claim 3, wherein the growth substrate is a cereal grain of a particle size in the range of 0.1 to 5 mm.

9. A composition according to claim 4, additionally comprising glyphosate in an amount of 0.02 to 0.06% v/v.

10. A method for combating weeds of the Rubus species, comprising applying thereto, an effective amount of a herbicidal composition containing as active ingredient, a biologically pure isolate of *Fusarium avenaceum*, having all of the identifying characteristics of ATCC Deposit no. 200684.

11. A method according to claim 10, wherein the active ingredient is provided as an aqueous suspension of an agriculturally acceptable sterile growth substrate inoculated therewith, and an adjuvant, included in an amount of 0.2 to 0.4% v/v.

12. A method according to claim 11, wherein the adjuvant is an organosilicone surfactant.

13. A method according to claim 12, wherein the amount is about 0.4% v/v.

14. A method according to claim 10, wherein the composition is applied to the weed, post emergence, as a foliar spray.

15. A method according to claim 11, wherein the aqueous suspension comprises about 5 g of inoculated substrate per 50 ml of water.

16. A method according to claim 15, wherein the aqueous suspension is applied in an amount of about 50 $ml/m^2$, post emergence, as a foliar spray.

17. A method according to claim 11, wherein the weed is *Rubus strigosus* or *Rubus parviflorus.*

18. A method according to claim 11, wherein the growth substrate is rice.

19. A method according to claim 11, wherein the composition additionally comprises glyphosate in an amount of 0.02 to 0.06% v/v.

* * * * *